US007559491B1

(12) United States Patent
Chang

(10) Patent No.: US 7,559,491 B1
(45) Date of Patent: Jul. 14, 2009

(54) ATOMIZER

(75) Inventor: Eric Chang, Taichung Hsien (TW)

(73) Assignee: Hsiner Co., Ltd., Taichung Hsien (TW)

( * ) Notice: Subject to any disclaimer, the term of this patent is extended or adjusted under 35 U.S.C. 154(b) by 0 days.

(21) Appl. No.: 11/969,337

(22) Filed: Jan. 4, 2008

(51) Int. Cl.

| | |
|---|---|
| ***A61M 11/06*** | (2006.01) |
| ***A61M 11/00*** | (2006.01) |
| ***B05B 7/30*** | (2006.01) |
| ***B05B 7/24*** | (2006.01) |
| ***B05B 7/28*** | (2006.01) |
| ***B05B 1/26*** | (2006.01) |

(52) U.S. Cl. ....................... 239/338; 239/346; 239/432; 128/200.18; 128/200.21

(58) Field of Classification Search ................. 239/302, 239/310, 311, 318, 337, 338, 340, 343, 346, 239/350, 369–371, 432, 433, 434.5; 128/200.12, 128/200.14, 200.18, 200.21
See application file for complete search history.

(56) References Cited

U.S. PATENT DOCUMENTS 3,762,409 A * 10/1973 Lester ................... 128/200.14
4,588,129 A * 5/1986 Shanks ....................... 239/338
5,503,139 A * 4/1996 McMahon et al. ..... 128/200.18
5,533,497 A * 7/1996 Ryder ................... 128/200.21
6,338,443 B1 * 1/2002 Piper .......................... 239/340
2004/0031485 A1 * 2/2004 Rustad et al. .......... 128/200.18

* cited by examiner

*Primary Examiner*—Darren W Gorman
(74) *Attorney, Agent, or Firm*—Darby & Darby P.C.

(57) ABSTRACT

An atomizer includes: an enclosed reservoir defining an inner space adapted to receive a liquid therein; a jet nozzle provided in the inner space for passage of an air jet therethrough; a jacket sleeved around the jet nozzle to define a fluid-introducing gap therebetween, the fluid-introducing gap being in fluid communication with the inner space for passage of the liquid therethrough; a mist-discharging conduit extending sealingly into and in fluid communication with the inner space and aligned with the jacket in a jet-ejecting direction; and a compressible member connected to the mist-discharging conduit and the jacket and compressible in the jet-ejecting direction. The jacket, the compressible member, and the mist-discharging conduit are an integrally formed single piece.

7 Claims, 5 Drawing Sheets

ATOMIZER

BACKGROUND OF THE INVENTION

1. Field of the Invention

This invention relates to an atomizer.

2. Description of the Related Art

As shown in FIGS. 1 and 2, a conventional atomizer includes a container 1 having a jet nozzle 101 defining an air passage 102 therein; a jacket 2 sleeved around the jet nozzle 101 of the container 1 so as to define a gap 201 therebetween, and having an opening 202 in fluid communication with the air passage 102, and a jet-blocking plate 203 disposed above the opening 202; and a cap 3 having a mist path 302 defined by a peripheral wall 301 and a blocking wall 303 connected to the peripheral wall 301. During assembling, the jacket 2 is sleeved around the jet nozzle 101 of the container 1, and the cap 3 is secured to the container 1 so that the blocking wall 303 of the cap 3 abuts against the jet-blocking plate 203 of the jacket 2. In use, when high-pressure air (50 psi) flows through the air passage 102, a fluid contained in the container 1 will flow through the gap 201 between the jacket 2 and the jet nozzle 101 because of a negative pressure generated in the air passage 102. The fluid flowing through the gap 201 will be atomized by the high-pressure air. The mist thus formed flows into the mist path 302 through the opening 202.

Although the conventional atomizer can achieve an atomizing function, there are certain drawbacks in practice.

Since the jet nozzle 101, the jacket 2, and the cap 3 are separate parts, a high precision is required to manufacture these parts so as to ensure appropriate abutment between the blocking wall 303 of the cap 3 and the jet-blocking plate 203 of the jacket 2, and so as to prevent relative movement between the jacket 2 and the jet nozzle 101, which can result in a poor atomizing effect.

In addition, since the container 1, the jacket 2, and the cap 3 are three individual parts, costs for manufacturing the atomizer are increased, and the manufacturing process is relatively complicated. Moreover, since the jacket 2 is relatively small in size, it is likely to be misplaced.

SUMMARY OF THE INVENTION

Therefore, the object of the present invention is to provide an atomizer that can overcome the aforesaid drawbacks of the prior art.

According to this invention, an atomizer includes an enclosed reservoir defining an inner space adapted to receive a liquid therein, a jet nozzle provided in the inner space for passage of an air jet therethrough, a jacket sleeved around the jet nozzle to define a fluid-introducing gap therebetween, the fluid-introducing gap being in fluid communication with the inner space for passage of the liquid therethrough, a mist-discharging conduit extending sealingly into and in fluid communication with the inner space for passage of a mist therethrough and aligned with the jacket in a jet-ejecting direction, and a compressible member connected to the mist-discharging conduit and the jacket and compressible in the jet-ejecting direction so as to retain the jacket at a predetermined position. The jacket, the compressible member, and the mist-discharging conduit are an integrally formed single piece.

BRIEF DESCRIPTION OF THE DRAWINGS

Other features and advantages of the present invention will become apparent in the following detailed description of the preferred embodiment of this invention, with reference to the accompanying drawings, in which.

DETAILED DESCRIPTION OF THE PREFERRED EMBODIMENT

Figure 1:
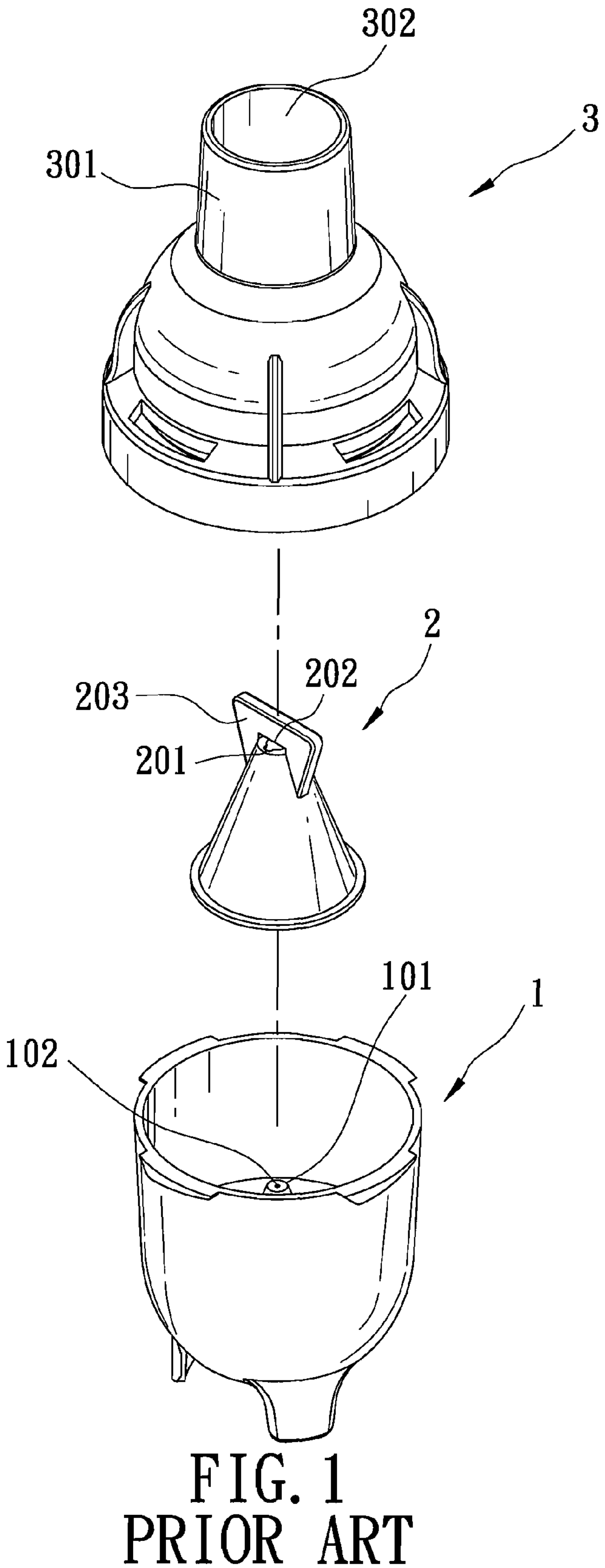
FIG. 1 PRIOR ART
FIG. 1 is an exploded perspective view of a conventional atomizer.
Figure 2:
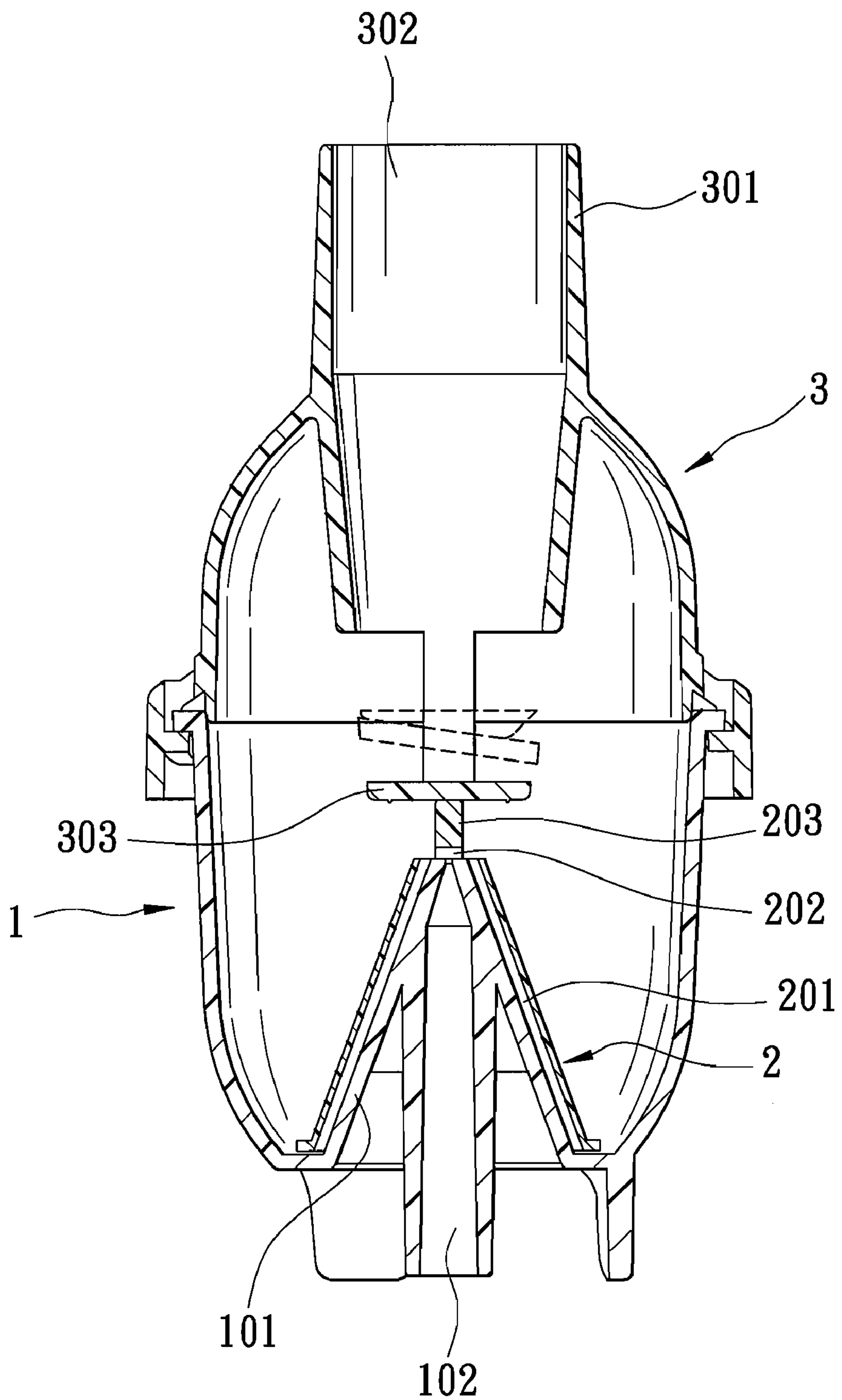
FIG. 2 PRIOR ART
FIG. 2 is an assembled cross-sectional view of the conventional atomizer shown in FIG. 1.
Figure 3:
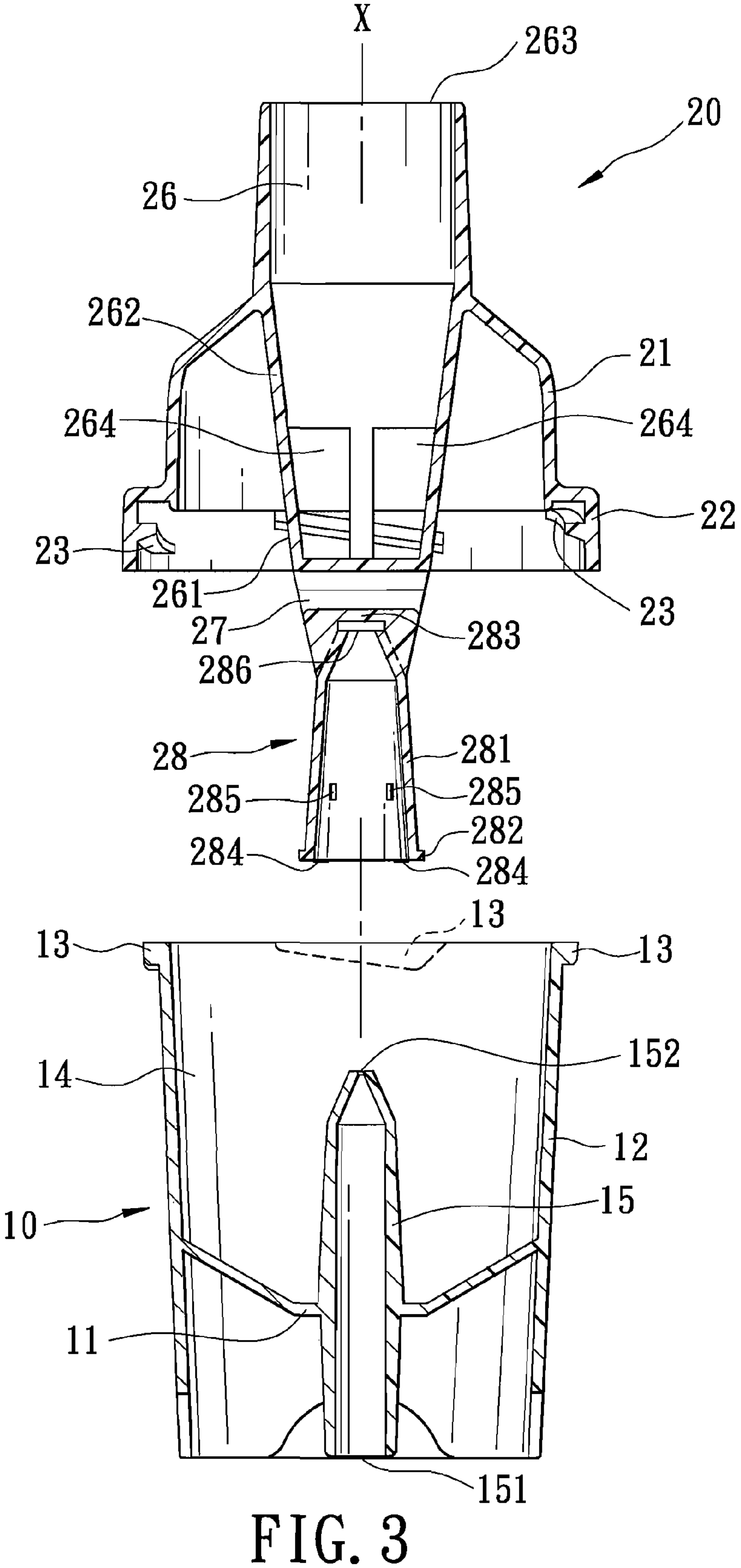
FIG. 3 is an exploded cross-sectional view of the preferred embodiment of an atomizer according to this invention.
Figure 4:
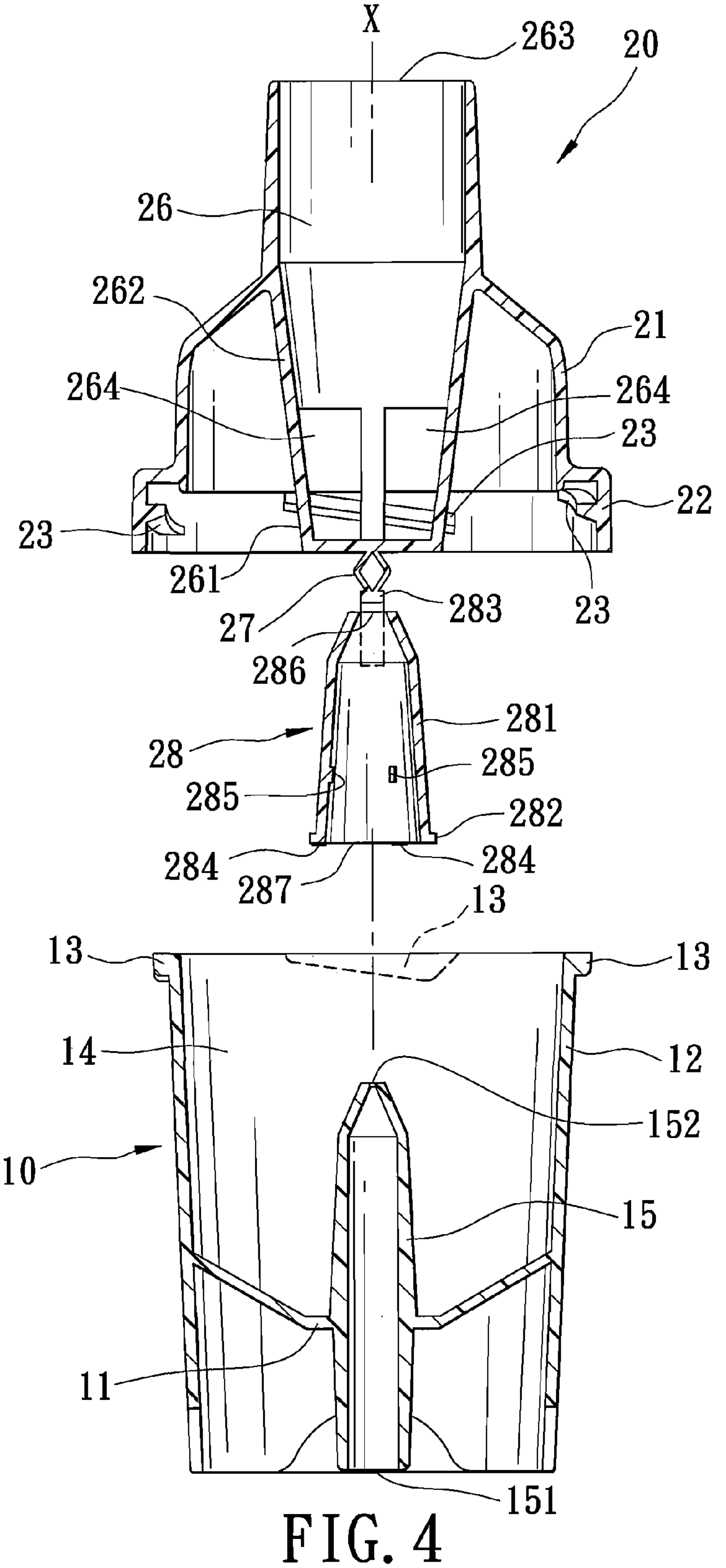
FIG. 4 is an exploded cross-sectional view of the preferred embodiment when viewed from another angle.
Figure 5:
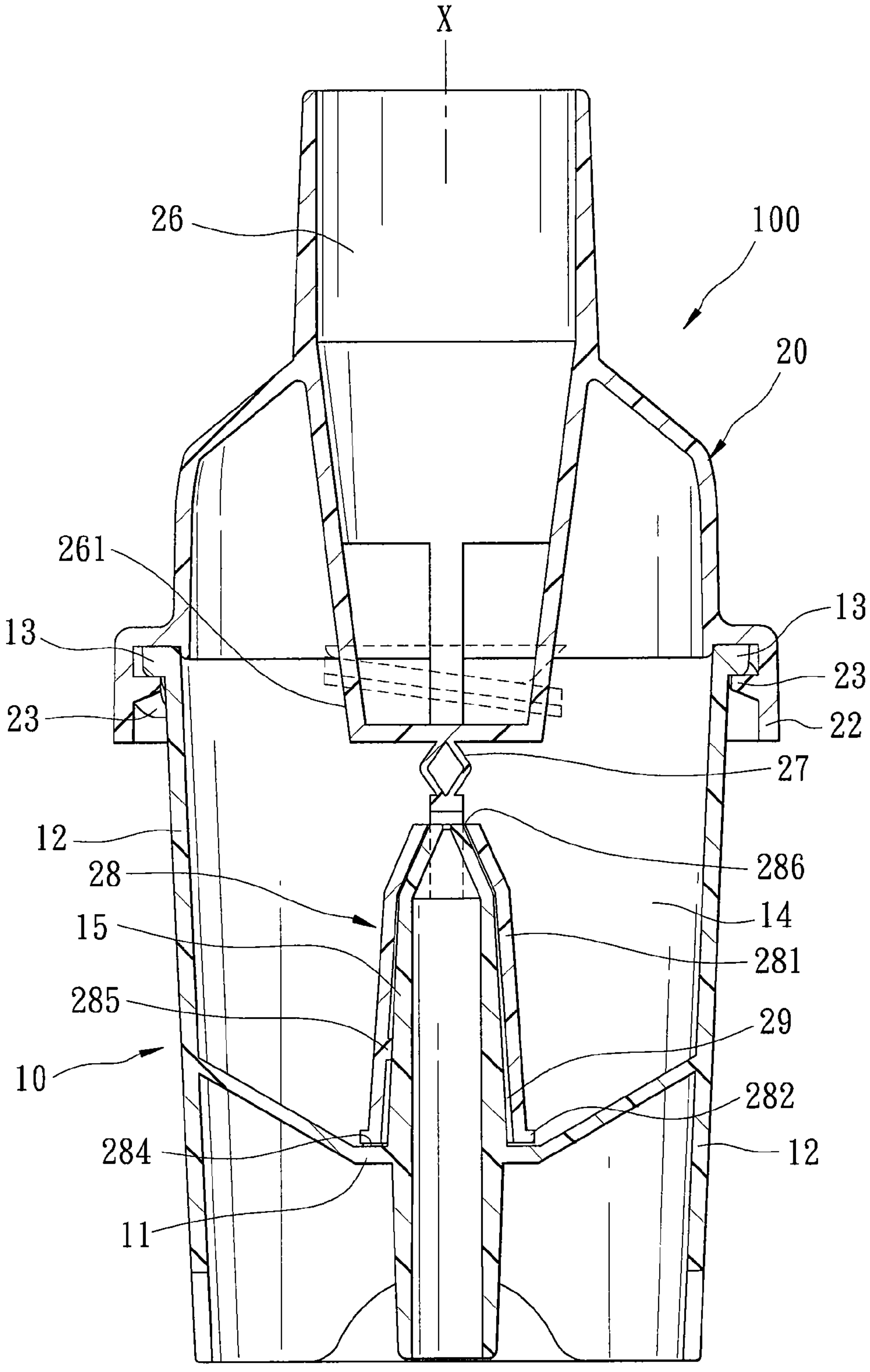
FIG. 5 is an assembled cross-sectional view of the preferred embodiment.

Referring to FIGS. 3 to 5, the preferred embodiment of an atomizer according to the present invention is shown to include an enclosed reservoir 100 defining an inner space 14 adapted to receive a liquid (e.g., a liquid medication) therein, a jet nozzle 15 provided in the inner space 14 for passage of an air jet therethrough, a jacket 28 sleeved around the jet nozzle 15 to define a fluid-introducing gap 29 therebetween, a mist-discharging conduit 26, and a compressible member 27 connected to the mist-discharging conduit 26 and the jacket 28.

Specifically, the enclosed reservoir 1 includes a container 10 and a cap 20 connected detachably and securely to the container 10. The container 10 includes a surrounding wall 12 and a partition wall 11 extending from the surrounding wall 12 to the jet nozzle 15 and confining a bottom side of the inner space 14. The surrounding wall 12 is formed with a plurality of engaging flanges 13, each of which extends radially and outwardly from a top periphery of the surrounding wall 12.

The jet nozzle 15 extends sealingly in a jet-ejecting direction (X) through the partition wall 11 and into the inner space 14. The jet nozzle 15 includes an air inlet 151 and a tapered air outlet 152.

The cap 20 includes a peripheral wall 21 and is formed with a plurality of engaging parts 23 on an inner side of a periphery 22 of the peripheral wall 21. The engaging parts 23 of the cap 20 engage the engaging flanges 13 of the surrounding wall 12 of the container 10, respectively, so as to secure the cap 20 to the container 10.

The mist-discharging conduit 26 extends sealingly into and is in fluid communication with the inner space 14 for passage of a mist therethrough, and is aligned with the jacket 28 in the jet-ejecting direction (X). The mist-discharging conduit 26 includes a lower wall 261 and an upper wall 262 extending from the lower wall 261. The mist-discharging conduit 26 is formed with an opening 263 in an end of the upper wall 262 opposite to the lower wall 261, and a plurality of mist-guiding holes 264 in the lower wall 261. The upper wall 262 of the mist-discharging conduit 26 is connected to the peripheral wall 21 of the cap 20. In this embodiment, the cap 20 and the mist-discharging conduit 26 are an integrally formed single piece.

The jacket 28 has a surrounding wall 281 extending in the jet-ejecting direction (X), and an end flange 282 extending radially and outwardly from the surrounding wall 281. The surrounding wall 281 and the end flange 282 are provided with spaced apart spacers 285 that abut against the jet nozzle 15 and spaced apart spacers 284 that abut against the partition wall 11, respectively, so as to form the fluid-introducing gap 29 between the jet nozzle 15 and the jacket 28. The fluid-introducing gap 29 is in fluid communication with the inner space 14 for passage of the liquid therethrough. The jacket 28 further includes a tapered end that defines a restricted opening 286 and that is provided with a jet-blocking member 283 having a portion disposed adjacent to and aligned with the restricted opening 286 in the jet-ejecting direction (X) so as to block the air jet from the jet nozzle 15 and the liquid flow from the fluid-introducing gap 29.

Preferably, the compressible member 27 is disposed between a bottom of the lower wall 261 of the mist-discharging conduit 26 and a top of the jet-blocking member 283, and is compressible in the jet-ejecting direction (X) so as to retain the jacket 28 at a predetermined position. In this invention, the jacket 28, the compressible member 27, and the mist-discharging conduit 26 are an integrally formed single piece. Preferably, the compressible member 27 is in the form of a hollow body that has a rhombic cross-section (see FIGS. 4 and 5).

In use, when a high-pressure air jet passes through the jet nozzle 15 from the air inlet 151 to the air outlet 152, the liquid (not shown) in the inner space 14 flows through the fluid-introducing gap 29 because of a negative pressure generated in the fluid-introducing gap 29, and hits the jet-blocking member 283. The high-pressure air atomizes the liquid as the liquid leaves the restricted opening 286. The mist then flows into the mist-discharging conduit 26 through the mist-guiding holes 264.

According to the present invention, since the jacket 28, the compressible member 27, and the mist-discharging conduit 26 are an integrally formed single piece, costs for manufacturing the atomizer can be decreased, and the problem associated with misplacement of the jacket 28 in the conventional atomizer can be eliminated. Moreover, with the construction of integrally formed single piece and with the inclusion of the compressible member 27 in the present invention, the high precision requirement associated with the conventional atomizer can be eliminated.

While the present invention has been described in connection with what is considered the most practical and preferred embodiment, it is understood that this invention is not limited to the disclosed embodiment but is intended to cover various arrangements included within the spirit and scope of the broadest interpretation and equivalent arrangements.

What is claimed is:

1. An atomizer comprising:

an enclosed reservoir defining an inner space adapted to receive a liquid therein;

a jet nozzle provided in the inner space for passage of an air jet therethrough;

a jacket sleeved around the jet nozzle to define a fluid-introducing gap therebetween, the fluid-introducing gap being in fluid communication with the inner space for passage of the liquid therethrough;

a mist-discharging conduit extending sealingly into and in fluid communication with the inner space for passage of a mist therethrough and aligned with the jacket in a jet-ejecting direction; and a compressible member connected to and disposed between the mist-discharging conduit and the jacket and compressible in the jet-ejecting direction so as to retain the jacket at a predetermined position;

wherein the jacket, the compressible member, and the mist-discharging conduit are an integrally formed single piece.

2. The atomizer of claim 1, wherein the enclosed reservoir includes a container and a cap connected detachably and securely to the container, the cap and the mist-discharging conduit being an integrally formed single piece.

3. The atomizer of claim 1, wherein the compressible member is in the form of a hollow body that has a rhombic cross-section.

4. The atomizer of claim 2, wherein the enclosed reservoir is provided with a partition wall extending from the container to the jet nozzle and confining a bottom side of the inner space, the jet nozzle extending sealingly in the jet-ejecting direction through the partition wall and into the inner space, the jacket having a surrounding wall extending in the jet-ejecting direction and surrounding the jet nozzle, and an end flange extending radially and outwardly from the surrounding wall and provided with spaced apart spacers that abut against the partition wall.

5. The atomizer of claim 4, wherein the surrounding wall of the jacket is provided with spaced apart spacers that abut against the jet nozzle.

6. The atomizer of claim 1, wherein the jacket has a tapered end that defines a restricted opening and that is provided with a jet-blocking member having a portion disposed adjacent to and aligned with the restricted opening in the jet-ejecting direction so as to block the air jet from the jet nozzle and the liquid flow from the fluid-introducing gap.

7. An atomizer comprising:

an enclosed reservoir defining an inner space adapted to receive a liquid therein;

a jet nozzle provided in the inner space for passage of an air jet therethrough;

a jacket sleeved around the jet nozzle to define a fluid-introducing gap therebetween, the fluid-introducing gap being in fluid communication with the inner space for passage of the liquid therethrough, the jacket having a tapered end that defines a restricted opening and that is provided with a jet-blocking member having a portion disposed adjacent to and aligned with the restricted opening in the jet-ejecting direction so as to block the air jet from the jet nozzle and the liquid flow from the fluid-introducing gap;

a mist-discharging conduit extending sealingly into and in fluid communication with the inner space for passage of a mist therethrough and aligned with the jacket in a jet-ejecting direction; and a compressible member connected between the mist-discharging conduit and the jet-blocking member and disposed on one side of the jet-blocking member opposite to the restricted opening, the compressible member being compressible in the jet-ejecting direction so as to retain the jacket at a predetermined position relative to the jet nozzle.

* * * * *